US00PP18978P2

(12) United States Plant Patent
Jones

(10) Patent No.: US PP18,978 P2
(45) Date of Patent: Jun. 24, 2008

(54) ***NEMESIA* PLANT NAMED 'PENPUR'**

(50) Latin Name: *Nemesia fruitcans*
Varietal Denomination: Penpur

(76) Inventor: Sidney James Jones, Nurseries St. Brides, Netherwent Magor, Newport, Gwent NP6 3AU (GB)

( * ) Notice: Subject to any disclaimer, the term of this patent is extended or adjusted under 35 U.S.C. 154(b) by 94 days.

(21) Appl. No.: 11/523,299

(22) Filed: Sep. 18, 2006

(51) Int. Cl.
*A01H 5/00* (2006.01)

(52) U.S. Cl. ..... Plt./458

(58) Field of Classification Search ..... Plt./458
See application file for complete search history.

*Primary Examiner*—Kent L Bell

(57) ABSTRACT

A new and distinct cultivar of *Nemesia* plant named 'PENPUR' that is characterized by a compact habit and dense upright spikes of pure white flowers which do not exhibit a yellow palate on the lower petals. In combination, these characteristics set 'PENPUR' apart from all other existing varieties of *Nemesia* known to the inventor.

2 Drawing Sheets

Genus: *Nemesia*.
Species: *fruticans*.
Denomination: 'PENPUR'.

BACKGROUND OF THE INVENTION

The present invention relates to a new and distinct cultivar of *Nemesia* plant that will be referred to hereinafter by the cultivar name 'PENPUR'. 'PENPUR' was discovered by the inventor in 2000 at the inventor's nursery in Netherwent, Wales, United Kingdom.

In the summer of 2000, the inventor observed that a single plant of the inventor's blue flowered *Nemesia* variety named 'PENSKY' (U.S. Plant Pat. No. 16,902) was bearing a naturally occurring branch sport which carried pure white flowers. The inventor had previously observed white flowered *Nemesias* in his breeding program, and was also aware of white flowered *Nemesia* varieties in commerce. However all of these white flowered varieties known or observed by the inventor shared the common characteristic of a distinct yellow palate at the base of the lower petals. Such a yellow palate to generally present in *Nemesias* and appears as a raised area on each of the pair of lower petal lips, giving the appearance of a yellow throat.

The inventor was able to take several cuttings from the branch sport of 'PENSKY' and to observe each of the resulting plants as they came into flower. Each of the plants bore an identical pure white flower with no apparent yellow palate. The inventor determined that he had developed a new and distinct variety of *Nemesia,* named 'PENPUR' which remained true to type in successive generations of asexual reproduction.

The inventor has observed that if the upper and lower petals are prized apart then a small yellow palate is visible on the lower petal surfaces. However, when the petals are returned to their natural aspect, no yellow palate is visible to the observer.

When compared with the sport parent *Nemesia* 'PENSKY', 'PENPUR' differs only in respect of the color of its flowers and flower parts. In overall appearance, 'PENPUR' exhibits pure white flowers whereas 'PENSKY' exhibits soft pale lavender blue flowers.

The closest variety of white flowered *Nemesia* known to the inventor is *Nemesia* plant named 'Tiktoc' (U.S. Plant Pat. No. 10,977) sold as *Nemesia* 'Compact Innocence', which exhibits a prominent yellow palate on its lower petals.

'PENPUR' was first asexually propagated by the inventor at the inventor's nursery in Netherwent, Wales, United Kingdom in 2000 using internodal cuttings. 'PENPUR' has subsequently be asexually propagated, using tip and branch cuttings, and has been determined to reproduce true to type in successive generations of asexual reproduction.

SUMMARY OF THE INVENTION

The following traits have been repeatedly observed and represent the distinguishing characteristics of 'PENPUR'. In combination these traits set the new cultivar apart from all other existing varieties of *Nemesia* known to the inventor. 'PENPUR' has not been tested under all possible conditions and phenotype differences may be observed with variations in environmental, climatic, and cultural conditions, however, without any variance in genotype.

1. 'PENPUR' exhibits a compact habit.
2. 'PENPUR' exhibits pure white flowers.
3. The flowers of 'PENPUR' do not carry a visible yellow palate on the lower petals.
4. 'PENPUR' exhibits upright flower spikes.
5. 'PENPUR' is hardy to USDA Zone 9.

BRIEF DESCRIPTION OF THE DRAWINGS

The accompanying drawings illustrate the distinguishing traits and overall appearance of the new *Nemesia* cultivar 'PENPUR'. The plant photographed is one year old, and has been grown to flowering in a 9 cm container outdoor in Cambridgeshire, United Kingdom.

The drawing labeled as FIG. 1 illustrates the entire plant.

Figure 1:
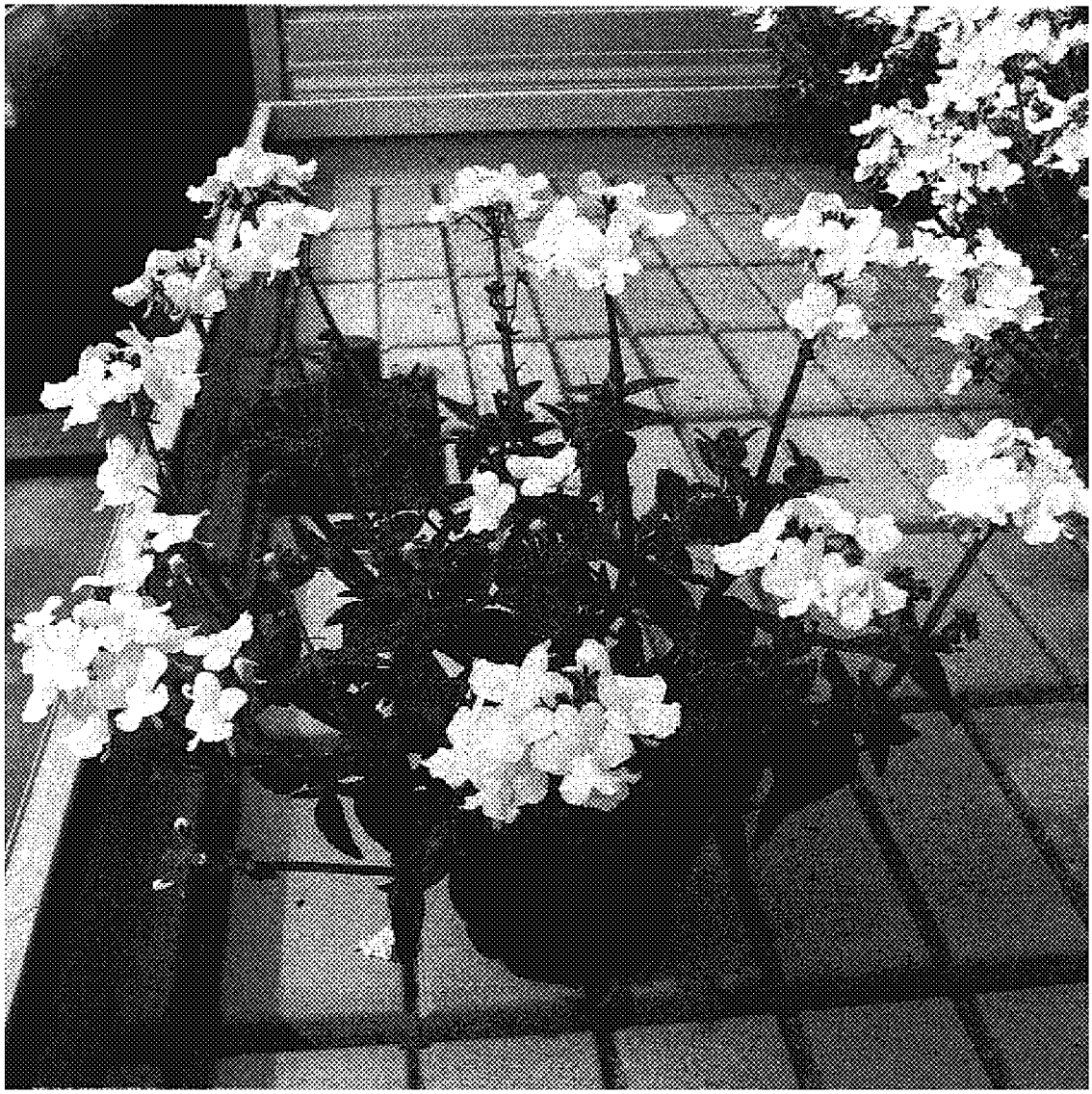
Figure 2:
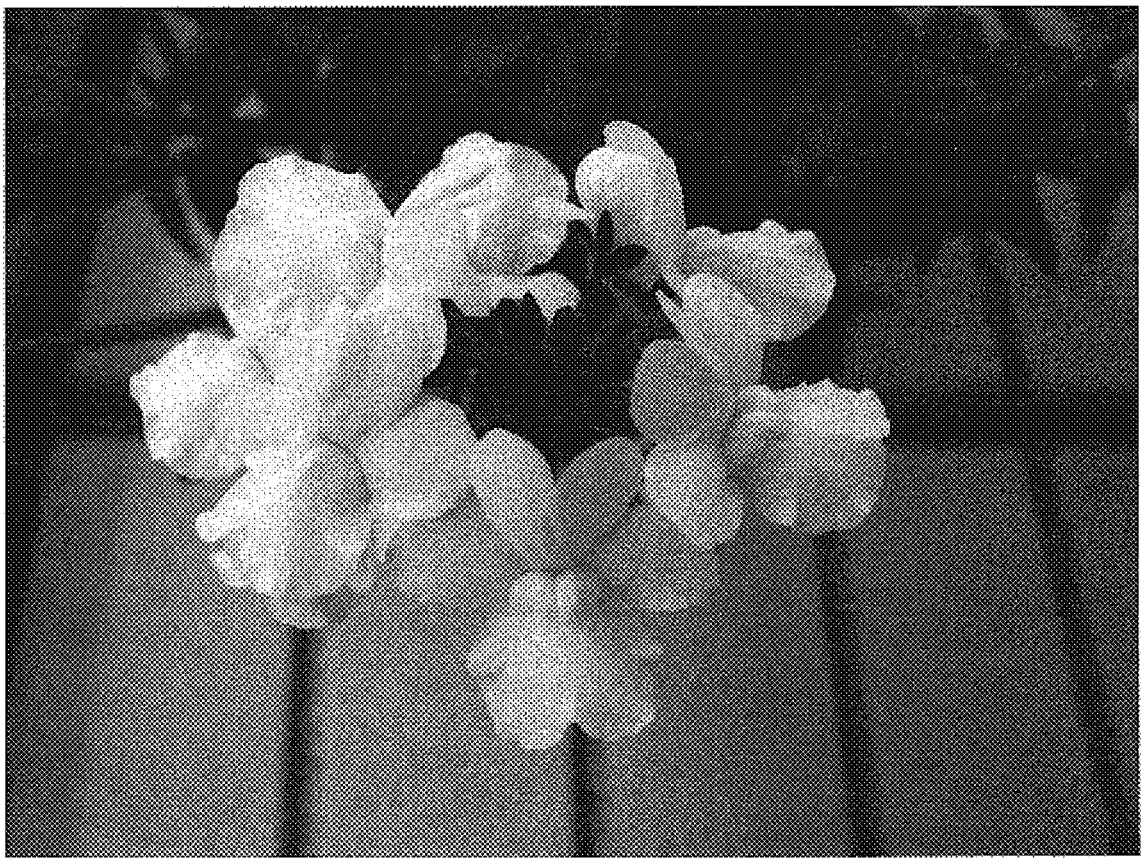

The drawing labeled as FIG. 2 presents a close-up of a single inflorescence.

The drawings were made using conventional photographic techniques and the laser copies were made using standard techniques. Although colors may appear different from actual colors due to light reflectance, they are as accurate as possible by conventional photography and laser copying.

BOTANICAL DESCRIPTION OF THE PLANT

The following is a detailed description of the *Nemesia* plant named 'PENPUR'. Data was collected in Cambridgeshire, United Kingdom from plants grown in 9 cm containers under greenhouse conditions. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other *Nemesia* plants.

Botanical classification: *Nemesia fruticans* 'PENPUR'.
Common name: *Nemesia*.
Use: Bedding and patio plant.
Parentage (sport parent): *Nemesia* 'PENSKY', U.S. Plant Pat. No. 16,902.
Propagation: Vegetative cuttings.
Sexuality: Hermaphrodite.
Vigor: Average.
Growth habit: Compact habit.
Plant dimensions: 25 cm in height and 25 cm in width.
Type: Annual or Perennial in USDA Zones 9.
Time to initiate roots; Approximately 14 days at temperatures of 18° Centigrade is required to produce rooted cuttings.
Crop time: 21 days are required to reach commercial size from a rooted cutting.
Culture requirements: Moderately fertile soil in semi-shade to full sun.
Uses: Pots, patio containers, planting in open border.
Pest and disease resistance or susceptibility: In common with *Nemesias* and annual bedding plants generally, PENPUR is susceptible to pests including aphids and red spider mites; and diseases including botrytis which may result from poor air circulation. PENPUR has not been observed to exhibit any particular resistance or susceptibility to pests and diseases.
Root system: Numerous and fine.
Hardiness: Hardy to USDA Zone 9.
Stem:
*Shape.*—Square, angles slightly winged.
*Dimensions.*—25 cm in length and 2 mm in diameter.
*Surface.*—Glabrous.
*Color.*—143C.
*Lateral shoot angle at emergence.*—Angle acute — approximate 30°.
*Internode length.*—3 cm between nodes.
*Lenticles.*—Absent.
*Branching.*—Ascending and freely branching.
Foliage:
*Leaf shape.*—Ovate.
*Leaf division.*—Absent, leaf entire.
*Apex.*—Acute, but rounded at the extreme tip.
*Base.*—Rounded.
*Margins.*—Shallowly serrate.
*Surface.*—Glabrous.
*Arrangement.*—Opposite.
*Leaf dimension.*—3.5 cm in length and 2.0 cm in width.
*Leaf color* (*adaxial surface*).—137A.
*Leaf color* (*abaxial surface*).—138B.
*Vein color* (*adaxial surface*).—143A.
*Vein color* (*abaxial surface*).—141D.
*Attachment.*—Sessile.
*Vein pattern.*—Parallel.
*Fragrance.*—Absent.
Flowers:
*Flowering season.*—Spring and summer.
*Arrangement.*—Simple raceme, with further racemes emerging from axils of the upper leaves.
*Number of flowers per inflorescence.*—30, up to 8 open at any one time.
*Spacing in inflorescence.*—Very variable often with up to 6 flowers in an apparent whorl, but in other places up to 30 mm between flowers.
*Persistent or self-cleaning.*—Self-cleaning.
*Fragrance.*—Weak to moderate.
*Type.*—Single.
*Aspect.*—Facing upward at approximately 45°.
*Peduncle.*—Dimensions: 55 mm in length (below first flower) and 1.5 mm in diameter. Cross section: Square, angle slightly winged. Color: 143B. Pubescence: Moderately clothed with minute glandular hairs — too fine to color match.
*Pedicel color.*—143B.
*Pedicel pubescence.*—Moderately clothed with minute glandular hairs — too fine to color match.
*Bud.*—Dimensions: 8 mm in length and 6 mm in width. Shape: Cross-section trapezoid with the longest side at the bottom. Color: Pure, clear white — no true color match on the RHS Chart (nearest is 155C).
*Calyx.*—Dimensions: 2 mm in length and 7 mm in diameter. Pubescence: Moderately clothed with minute glandular hairs — too fine to color match. Number of sepals: 3.
*Sepal.*—Dimensions: 4 mm in length and 2 mm in width. Shape: Ovate-elliptic. Apex: Acute. Margin: Entire.
*Corolla.*—Shape: Strongly zygomorphic; overall height and width 19 mm. Number of petals/lobes: Divided into an entire lower lip and 4 lobes upper lip. Segments fused or free: Fused. Greatest overall diameter: 19 mm. Overall length: 12 mm. Length of tube: No obvious tube. Length of spur: 8 mm. Color of spur: 157D. Shape of lower lip: Broad obcordate, approximately 10 mm long and 12 mm broad. Margin of lower lip: Untoothed, moderately undulate. Color of inner surface of lower lip: Pure clear white; no true color match (nearest is 155C) with a very small patch of 8B near the base (only visible when lower and upper petals are prized apart). Color of outer surface of lower lip: Pure clear white; no true color match (nearest is 155C). Color of inner and outer surfaces of upper lip; Pure clear white; no true color match (nearest is 155C).
*Reproductive organs.*—Stamens: 4. Filament dimensions: Upper stamens 3 mm in length, lower stamens 1.5 mm in length; less than 0.5 mm in diameter. Filament color: Pure clear white; no true color match (nearest is 155C). Anther dimensions: Less than 1 mm in length and less than 0.5 mm in width. Anther color: 10B. Anther shape: Ellipsoid. Pollen color: 10B. Pollen quantity: Copious. Pistils: 1. Stigma and style shape: Unlobed. Stigma and style dimensions: 1 mm in length and less than 0.5 mm in width.

Stigma and style color: Very pale greenish white, too small to color match. Ovary shape: Ovate in longitudinal section, laterally flatted. Ovary position: Superior. Ovary dimensions: 1.5 mm in length and 1 mm in width. Ovary color: 144C.

Seed production:

*Quantity of seed.*—Approximately 6.

*Shape.*—Ellipsoid, surrounded longitudinal by a disc-like, papery wing.

*Color.*—199D, wing nearest to 156D.

*Dimensions.*—2 mm in length, 1 mm in width excluding wing.

It is claimed:

1. A new and distinct of *Nemesia* plant named 'PENPUR' as described and illustrated herein.

* * * * *